(12) United States Patent
Summers et al.

(10) Patent No.: US 8,470,975 B2
(45) Date of Patent: Jun. 25, 2013

(54) COLLAGEN MIXTURE AND METHOD OF MAKING THE SAME

(75) Inventors: Dana Summers, Sioux Center, IA (US); Robert den Hoed, Sioux Center, IA (US)

(73) Assignee: Robert den Hoed, Sioux Center, IA (US)

( * ) Notice: Subject to any disclaimer, the term of this patent is extended or adjusted under 35 U.S.C. 154(b) by 0 days.

(21) Appl. No.: 13/562,653

(22) Filed: Jul. 31, 2012

(65) Prior Publication Data

US 2013/0035473 A1 Feb. 7, 2013

Related U.S. Application Data

(62) Division of application No. 13/197,318, filed on Aug. 3, 2011.

(51) Int. Cl.
*A61K 38/17* (2006.01)

(52) U.S. Cl.
USPC .......................................................... 530/356

(58) Field of Classification Search
None
See application file for complete search history.

(56) References Cited

U.S. PATENT DOCUMENTS

| | | | |
|---|---|---|---|
| 6,838,440 B2 | 1/2005 | Stiles | |
| 6,899,294 B2 | 5/2005 | MacNeil | |
| 7,007,806 B2 | 3/2006 | MacNeil | |
| 7,584,909 B2 | 9/2009 | Vlad | |
| 2003/0209617 A1* | 11/2003 | MacNeil | 241/24.12 |
| 2004/0166213 A1* | 8/2004 | Thoroski | 426/298 |
| 2004/0253678 A1 | 12/2004 | Hasaio et al. | |
| 2007/0017447 A1 | 1/2007 | Vlad | |
| 2007/0178170 A1* | 8/2007 | DeVore et al. | 424/581 |
| 2008/0234195 A1* | 9/2008 | Long et al. | 514/12 |
| 2009/0104173 A1 | 4/2009 | Strohbehn et al. | |

* cited by examiner

*Primary Examiner* — Suzanne M Noakes
(74) *Attorney, Agent, or Firm* — Zarley Law Firm, P.L.C.

(57) ABSTRACT

A collagen mixture having a portion of unhydrolyzed eggshell membrane collagen and Avian collagen.

8 Claims, 4 Drawing Sheets

COLLAGEN MIXTURE AND METHOD OF MAKING THE SAME

CROSS REFERENCE TO A RELATED APPLICATION

This application is a division of U.S. Ser. No. 13/197,318 filed Aug. 3, 2011.

BACKGROUND OF THE INVENTION

This invention is directed to creating a collagen mixture and more specifically, without limitation, creating a collagen mixture of unhydrolyzed eggshell membrane with LOS with Avian collagen.

Methods for producing collagen are known in the art. Such collagen is used for many things such as the healing of wounds, the production of skin creams and shampoo, the treatment of osteoarthritis and osteoporosis, and as an additive for human and pet food. While useful, the process is expensive, complicated, involving many steps, and requires harsh chemicals and inorganics which can damage unique properties. Accordingly, a method and mixture is needed in the art that addresses these deficiencies.

An objective of the present invention is to combine Type I, V, and X collagen with Type II collagen.

Another objective of the present invention is to provide a method of making unhydrolyzed eggshell membrane collagen with LOS that involves fewer steps and is unde-natured.

A still further objective of the present invention is to provide a method of producing Avian collagen Type II with a greater molecular weight.

These and other objectives will be apparent to one of ordinary skill in the art based upon the following written description, drawings, and claims.

SUMMARY OF THE INVENTION

A collagen mixture includes a portion of unhydrolyzed eggshell membrane collagen and a portion of Avian collagen. The method of making the eggshell membrane collagen includes separating a membrane from an eggshell, drying the membrane, and pulverizing the membrane into a powder. The method of making the Avian collagen includes adding an enzyme mixture to a thawed Avian cartilage to break the cartilage down into liquid form, heating the liquid cartilage to form a layer of liquid digest, raising the pH level of the liquid digest, heating the raised pH level liquid digest to form a partial solid content, and spray drying the partial solid content.

DETAILED DESCRIPTION OF THE PREFERRED EMBODIMENT

Figure 1:
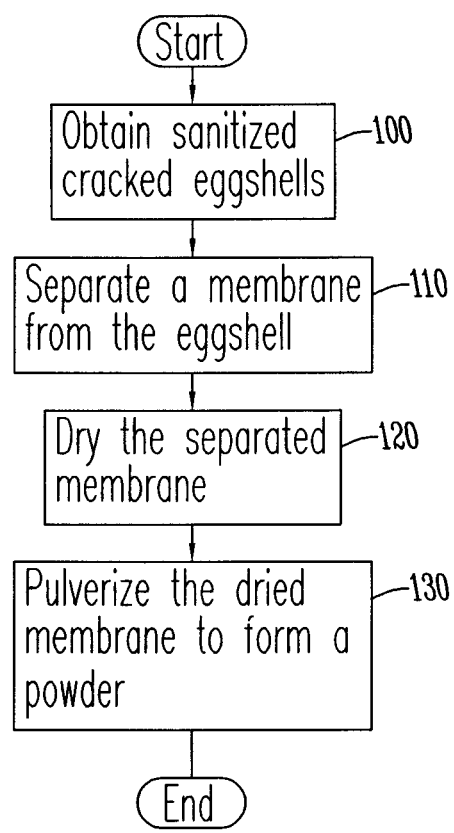
FIG. 1 is a flow diagram of a method for making unhydrolyzed eggshell membrane collagen.
Figure 2:
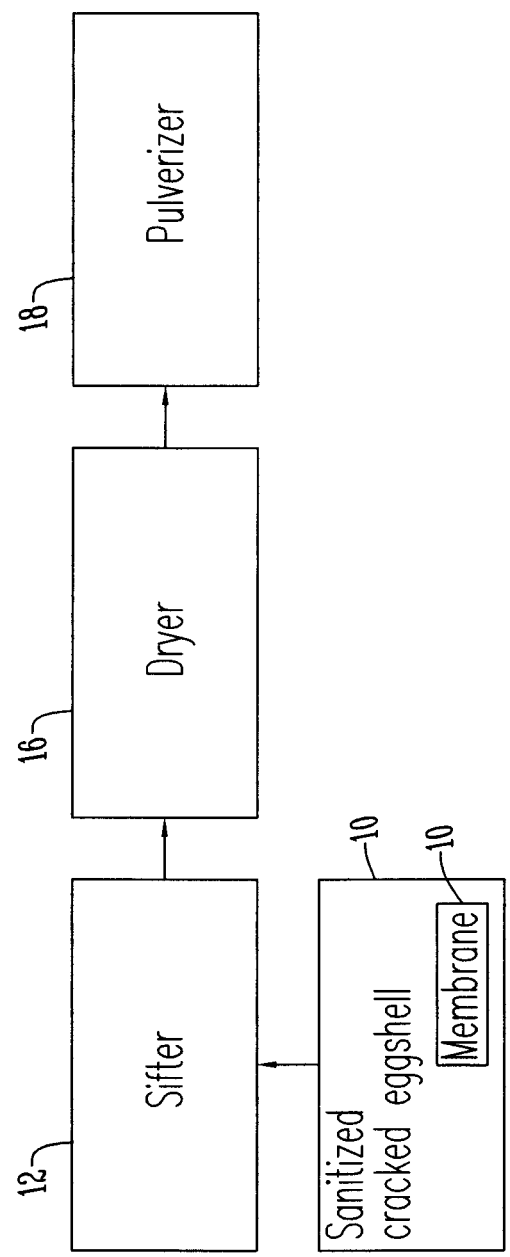
FIG. 2 is a schematic diagram of the environment for making unhydrolyzed eggshell membrane collagen.
Figure 3:
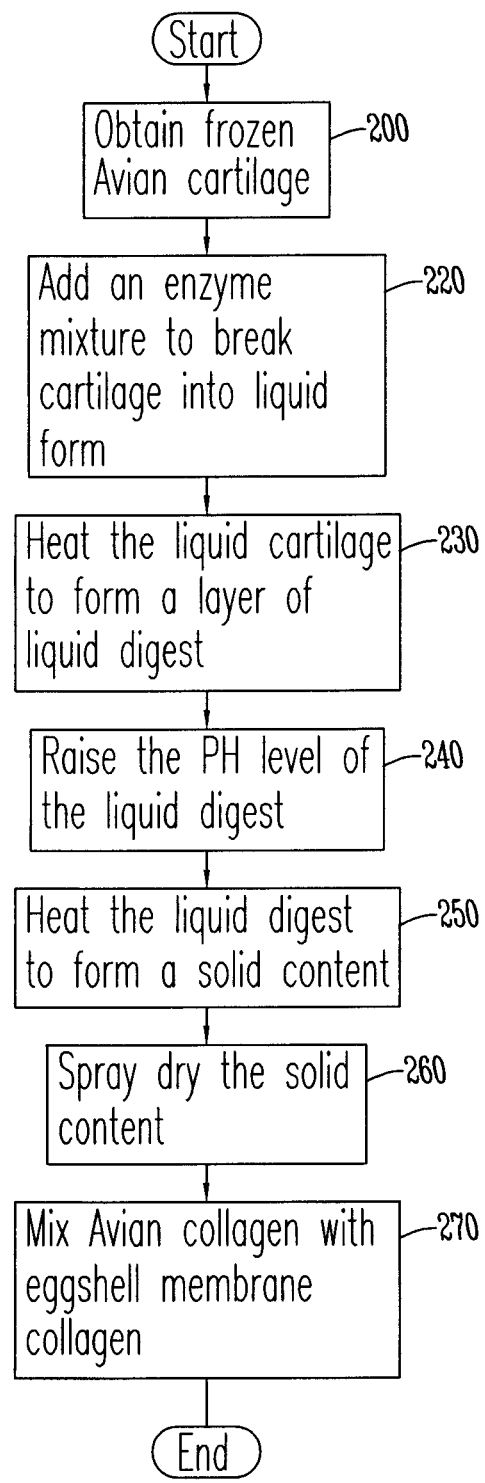
FIG. 3 is a flow diagram for a method of making a collagen mixture.
Figure 4:
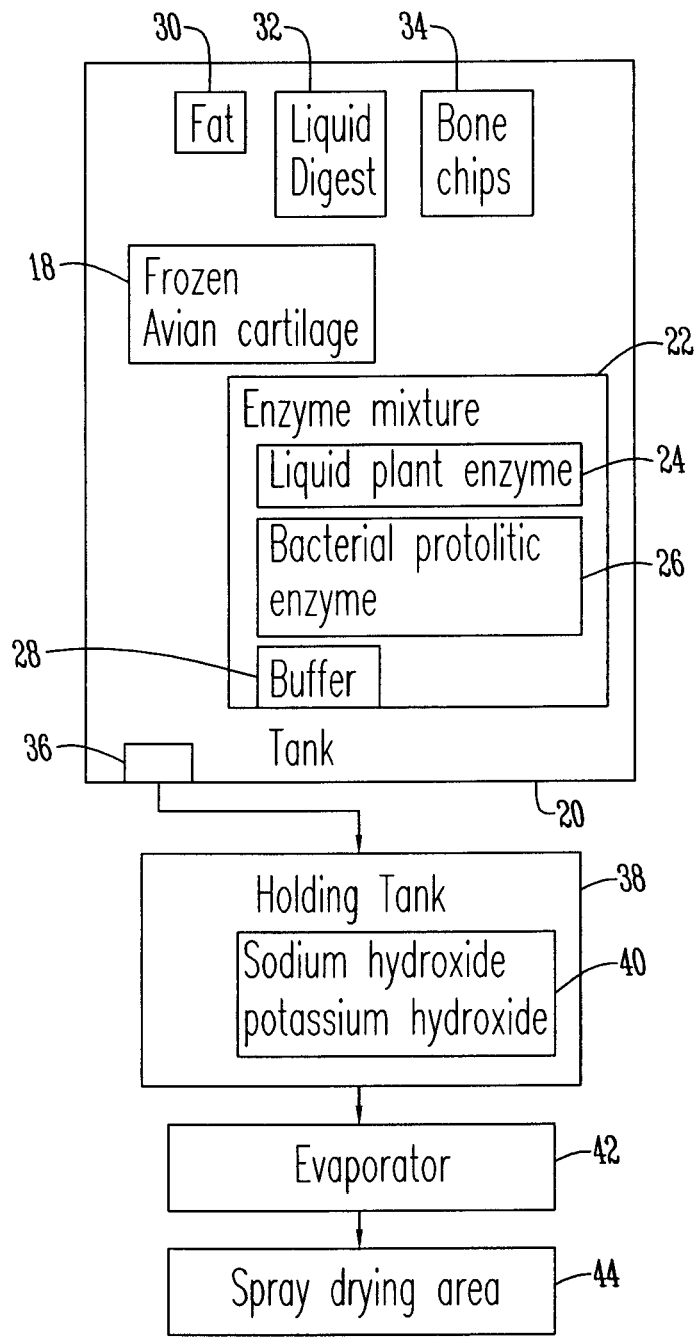
FIG. 4 is a schematic diagram of the environment for making a collagen mixture.

Referring to the Figures, the process of making unhydrolyzed eggshell membrane collagen containing Type I, V, and X collagen and lysosyme, ovatransferin, and sialic acid (LOS) begins at step 100 by obtaining sanitized cracked eggshells 10. The cracked eggshells 10 are placed on a sifter 12 at step 110 where the membrane 14 of the eggshell 10 is separated from the shell 10. The sifter 12 is of any type and preferably includes a fine mesh through which the shell 10 falls while the membrane 14 is transported to the end of the sifter 12.

Once separated, the membrane 14 is placed in a hot dryer 16 to dry the membrane and kill bacteria at step 120. While the dryer 16 is of any type, a motion dryer is preferred to facilitate faster drying. Once dried, the membrane 14, which is in flake form, is pulverized into a powder at step 130. Once in powder form, the membrane is packaged preferably in a fiber drum or bag for further use and/or processing.

The process of making the Avian collagen with LOS begins by obtaining Avian cartilage 18, typically in frozen form at step 200. At step 210, the frozen cartilage 18 is thawed by placing the cartilage in a tank 20 containing hot water. Once thawed, an enzyme mixture 22 is added to the thawed cartilage 18 which breaks the cartilage down into liquid form at step 220. Preferably, the enzyme mixture 22 includes a liquid plant derived enzyme 24 such as papain, ficen, or bromalain; a bacterial protolitic enzyme 26, such as acid, neutral, or alkelian; and a buffer 28 such as acetic acid or sodium hydroxide and water for a pH buffering range of 4.8 to 6.8. As the enzyme mixture 22 breaks down the cartilage 18, the tank is heated to preferably 140° -160° F. such that the cartilage 18 separates into a top layer of fat 30, a middle layer of liquid digest 32, and a bottom layer of bone chips 34.

Once separated, at step 230, the bone chips 34 are swept away from a valve 36 in the bottom of the tank 20 and the liquid digest 32 is pumped through the valve 36 to a holding tank 38. Once pumped, at step 240, the pH level of the liquid digest 32 is raised by adding sodium hydroxide or potassium hydroxide 40 to the liquid digest 32 in the holding tank 38. Preferably the pH level of the liquid digest 32 is raised to a level of 8 to 11.

At step 250, after the pH level is raised, the liquid digest 32 is pumped into an evaporator 42 where the liquid digest 32 is heated to a solid content of between 10% to 75% such that the liquid has a syrup consistency. Preferably the liquid digest is heated at a temperature of 200°-230° F. to create a solid content of 35-40%.

Next, at step 260, the solid liquid digest 32 is transported to an area for spray drying 44. Preferably, the solid liquid digest is spray dried using pulse combustion. Also, a carrier such as multrodextrine is added to assist in pulling off extra water from the liquid digest 32. This results in a dry powder comprised of Avian collagen.

Once the Avian collagen has been spray dried it is mixed with the unhydrolyzed eggshell membrane collagen at step 270 to create a blended collagen mixture that includes Type I, II, III, IV, V and X collagen and LOS. Preferably the mixture has 70% Avian collagen to 30% eggshell membrane or alternatively 30% Avian collagen to 70% eggshell membrane collagen. Once combined, at step 280, the mixture is packaged and distributed.

Accordingly, a collagen mixture and method of making the same has been disclosed that, at the very least, meets all the stated objectives.

What is claimed is:

1. A method of making collagen comprising the steps of:
   obtaining sanitized cracked eggshells;
   separating a membrane from the eggshell using a sifter having a fine mesh through which the eggshells fall while retaining the membrane;

drying the membrane after the membrane is separated from the eggshell; and pulverizing the dried membrane to form a powder.

2. The method of claim 1 wherein the membrane is dried using a motion dryer.

3. The method of claim 1 wherein the membrane is transported to an end of the sifter after it is separated from the eggshell.

4. The method of claim 1 wherein method results in unhydrolyzed eggshell membrane collagen.

5. The method of claim 1 wherein method results in unhydrolyzed eggshell membrane collagen with LOS (lysozyme, ovatransferin and sialic acid).

6. The method of claim 1 wherein the method results in eggshell membrane collagen having Type 1, V and X collagen.

7. The method of claim 1 wherein the eggshell membrane powder is Avian collagen.

8. The method of claim 1 wherein the eggshell membrane powder is combined with Type II collagen.

\* \* \* \* \*